(12) United States Patent
Tamai

(10) Patent No.: US 11,389,625 B2
(45) Date of Patent: Jul. 19, 2022

(54) MEDICAL NEEDLE

(71) Applicant: SB-KAWASUMI LABORATORIES, INC., Kanagawa (JP)

(72) Inventor: Yusuke Tamai, Oita (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 154 days.

(21) Appl. No.: 16/293,957

(22) Filed: Mar. 6, 2019

(65) Prior Publication Data

US 2019/0282785 A1 Sep. 19, 2019

Related U.S. Application Data

(60) Provisional application No. 62/642,166, filed on Mar. 13, 2018.

(51) Int. Cl.
*A61M 25/06* (2006.01)
*A61M 5/32* (2006.01)

(52) U.S. Cl.
CPC ...... *A61M 25/0637* (2013.01); *A61M 5/3245* (2013.01); *A61M 25/0631* (2013.01); *A61M 5/3257* (2013.01); *A61M 2205/273* (2013.01)

(58) Field of Classification Search
CPC .......... A61M 25/0637; A61M 25/0631; A61M 25/06; A61M 25/0606; A61M 25/0612; A61M 5/3245; A61M 5/158; A61M 5/322; A61M 5/3232; A61M 5/321; A61M 5/3257; A61M 2205/273
See application file for complete search history.

(56) References Cited

U.S. PATENT DOCUMENTS

| 5,676,658 | A | * | 10/1997 | Erskine | ............... | A61M 5/3269 |
| | | | | | | 604/165.03 |
| 6,090,078 | A | * | 7/2000 | Erskine | ............. | A61M 25/0631 |
| | | | | | | 128/919 |
| 2009/0131872 | A1 | * | 5/2009 | Popov | ............... | A61M 25/0625 |
| | | | | | | 604/164.08 |

FOREIGN PATENT DOCUMENTS

JP 2002-539897 A 11/2002
WO 00/57940 A1 10/2000

* cited by examiner

*Primary Examiner* — Tiffany Legette
*Assistant Examiner* — Antarius S Daniel
(74) *Attorney, Agent, or Firm* — Brundidge & Stanger, P.C.

(57) ABSTRACT

Provided is a medical needle that reduces a user's discomfort feeling while securely housing a needle tip into a case. Medical needle 1 includes needle portion 10 including needle tip 14 at the head thereof; case 30 configured to be capable of exposing needle portion 10 from the head thereof and housing the needle portion; movement mechanism 50 including spring member 60, which is located in case 30, configured to move needle portion 10 from a first position at which needle tip 14 protrudes from case 30 by a predetermined length to a second position at which needle tip 14 is housed in case 30; and curved portion 90 provided in a portion which is in movement mechanism 50 and faces case 30.

5 Claims, 10 Drawing Sheets

MEDICAL NEEDLE

CROSS REFERENCE TO RELATED APPLICATIONS

This application is entitled to and claims the benefit of U.S. provisional application Ser. No. 62/642,166 filed on Mar. 13, 2018, the disclosure of which is incorporated herein by reference in its entirety.

TECHNICAL FIELD

The present invention relates to a medical needle.

BACKGROUND ART

As a medical needle used for blood sampling, blood transfusion, fluid transfusion and the like, known is a medical needle having a cylindrical case provided with a spring member disposed therein (see, Patent Literature (hereinafter, referred to as PTL) 1, for example). Such conventional medical needles are capable of housing a needle tip that is in a state of being exposed from a case into the case by using a function of the spring member, and thus can prevent the occurrence of accidents such that people using the medical needles (including medical workers and patients: hereinafter referred to as "users") mistakenly pierce themselves with the used medical needles (also referred to as erroneous piercing).

CITATION LIST

Patent Literature

PTL 1
Japanese Unexamined Patent Application Publication (Translation of PCT Application) No. 2002-539897

SUMMARY OF INVENTION

Technical Problem

For securely housing a needle tip into a case, conventional medical needles uses a spring having relatively strong repulsion as a spring member in some cases. While the needle tip can be securely housed in the case, a needle housed in the case or the connection part of the needle bumps into the inner surface of the case, thereby causing rather strong impact and generating collision noise. Such an impact or sound may give a user a discomfort feeling.

The present invention is made for solving the above problem, and has an object to provide a medical needle capable of reducing a user's discomfort feeling while securely housing a needle tip into a case.

Solution to Problem (1) A medical needle (first medical needle) of the present invention includes a needle portion including a needle tip at the head thereof; a case configured to be capable of exposing the needle portion from a head thereof and housing the needle portion; a movement mechanism including an elastic member which is located in the case and configured to move the needle portion from a first position at which the needle tip protrudes from the case by a predetermined length to a second position at which the needle tip is housed in the case; and a curved portion which is provided in at least one of facing portions, namely a portion located in the movement mechanism and facing the case, a portion located in the needle portion and facing the case, and a portion located in the case and facing the movement mechanism or the needle portion, and which curves upon contact with the case, the movement mechanism or the needle portion.

(2) In the medical needle of the present invention, the elastic member is preferably a spring.

(3) In the medical needle of the present invention, it is preferably configured such that the movement mechanism further includes a control portion, and a fixing portion for fixing the control portion to the needle portion; and the case includes a first engagement portion for engagement with the control portion when the needle portion is positioned at the first position and a second engagement portion for engagement with the control portion when the needle portion is positioned at the second position, in which when the engagement of the first engagement portion with the control portion is released, the needle portion is moved from the first position to the second position by the elastic member, and the control portion engages with the second engagement portion.

(4) In the medical needle of the present invention, the control portion extends along the longitudinal direction of the case; at one end of the control portion, a protrusion capable of engaging with the first engagement portion or second engagement portion is provided; and at the other end of the control portion, the curved portion is located, in which the control portion is preferably configured such that the position of the protrusion is changeable toward the inner surface of the case by contact of the curved portion with the case.

(5) Another medical needle (second medical needle) of the present invention includes a needle portion including a needle tip at the head thereof; a case configured to be capable of exposing the needle portion from a head thereof and housing the needle portion; a movement mechanism including an elastic member which is located in the case and configured to move the needle portion from a first position at which the needle tip protrudes from the case by a predetermined length to a second position at which the needle tip is housed in the case; and another elastic member which is provided in at least one of facing portions, namely a portion located in the movement mechanism and facing the case, a portion located in the needle portion and facing the case, and a portion located in the case and facing the movement mechanism or the needle portion.

In the second medical needle of the present invention described in the above item (5), the features the same as in the medical needles of the present invention described in above items (2) to (4) can also be employed.

Advantageous Effects of Invention

As the medical needle of the present invention includes the above-mentioned curved portion, it is possible to reduce the impact caused by the contact between the case and the movement mechanism or needle portion, and also to suppress the generation of collision noise even when a spring having relatively strong repulsion is used as the elastic member.

As the second medical needle of the present invention includes another elastic member as described above, it is possible to reduce the impact caused by the contact between the case and the movement mechanism or needle portion, and also to suppress the generation of collision noise even when a spring having relatively strong repulsion is used as the elastic member.

Accordingly, the first and second medical needles of the present invention are each a medical needle capable of reducing a user's discomfort feeling while securely housing a needle tip into a case.

BRIEF DESCRIPTION OF DRAWINGS

FIG. 8A is a plan view of base 32, FIG. 8B is a sectional view of base 32 illustrated in FIG. 8A, taken along line C-C and FIG. 8C is a sectional view of base 32 illustrated in FIG. 8A, taken along line D-D;

FIG. 9A is a perspective view of control portion 70 and curved portion 90, FIG. 9B is a left side view of control portion 70 and curved portion 90 (viewed from X-direction illustrated in FIG. 9A) and FIG. 9C is a sectional view of control portion 70 and curved portion 90 illustrated in FIG. 9B, taken along line E-E;

FIG. 10A is a perspective view of fixing portion 80, FIG. 10B is a left side view of fixing portion 80 (viewed from X-direction illustrated in FIG. 10A) and FIG. 10C is a sectional view of fixing portion 80 illustrated in FIG. 10B, taken along line F-F;

FIG. 11A is a perspective view of movement mechanism 50 attached to needle portion 10 and FIG. 11B illustrates an inner structure of the periphery of movement mechanism 50 when needle portion 10 is at the first position;

FIG. 12A is a sectional view illustrating an inner structure of medical needle 1A when needle portion 10 is at the first position and FIG. 12B is a sectional view illustrating the inner structure of medical needle 1A when needle portion 10 is at the second position; FIG. 13A is a sectional view of medical needle 1B with cap 20B fit thereto and FIG. 13B is a sectional view of medical needle 1B with cap 20B removed therefrom.

DESCRIPTION OF EMBODIMENTS

Figure 1:
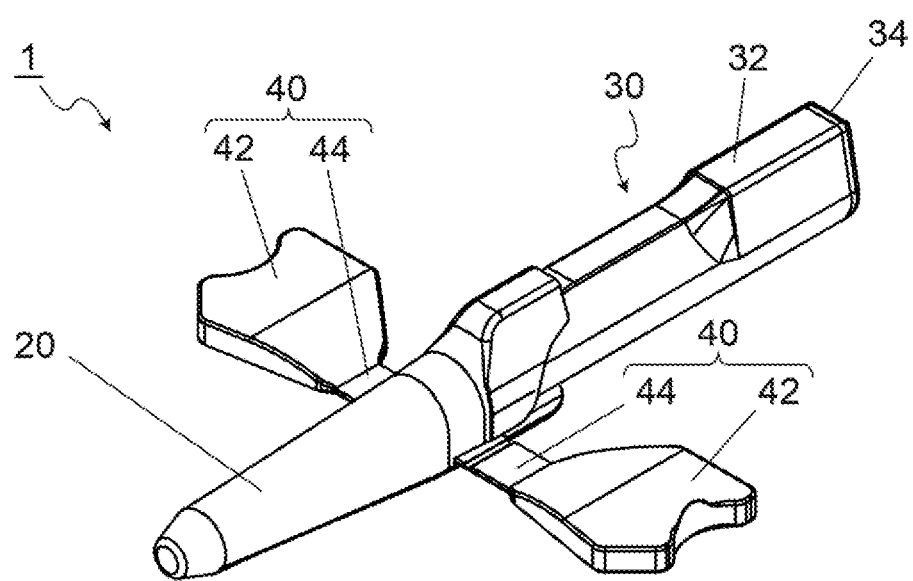
FIG. 1 is a perspective view of the whole of medical needle 1.

Hereinafter, the medical needle of the present invention will be described based on the embodiment illustrated in the drawings.

Embodiment

The whole configuration of medical needle 1 according to the embodiment and the configuration of each component will be described by using FIGS. 1 to 11B.

Figure 2:
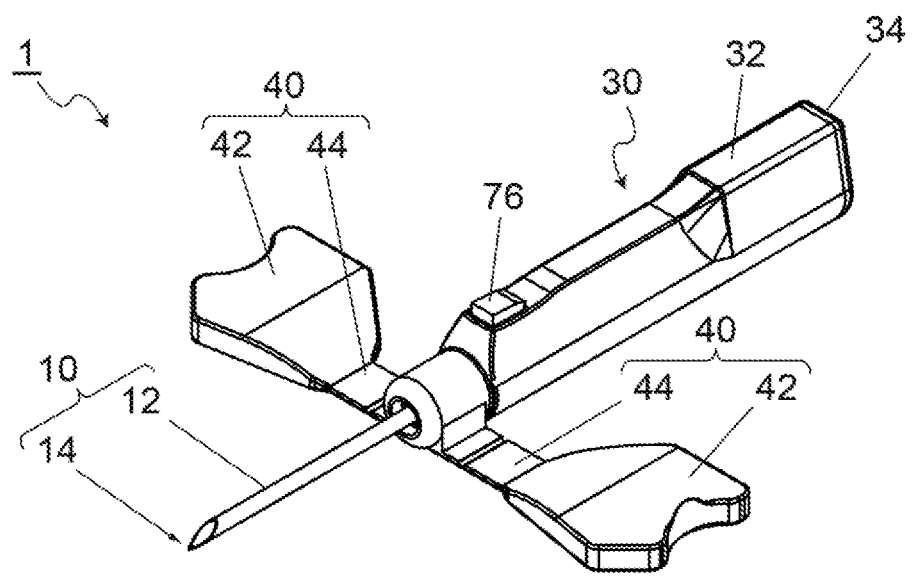
FIG. 2 a perspective view of the whole of medical needle 1 with cap 20 removed therefrom.
Figure 3:
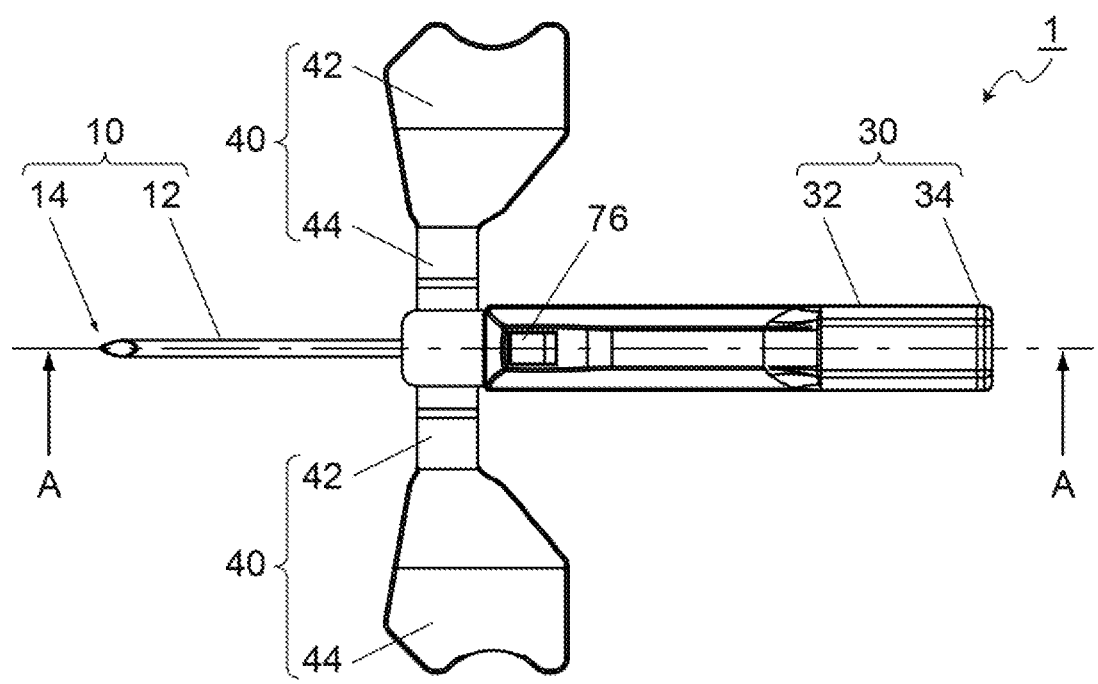
FIG. 3 is a plan view of medical needle 1 illustrated in FIG. 2.
Figure 4:
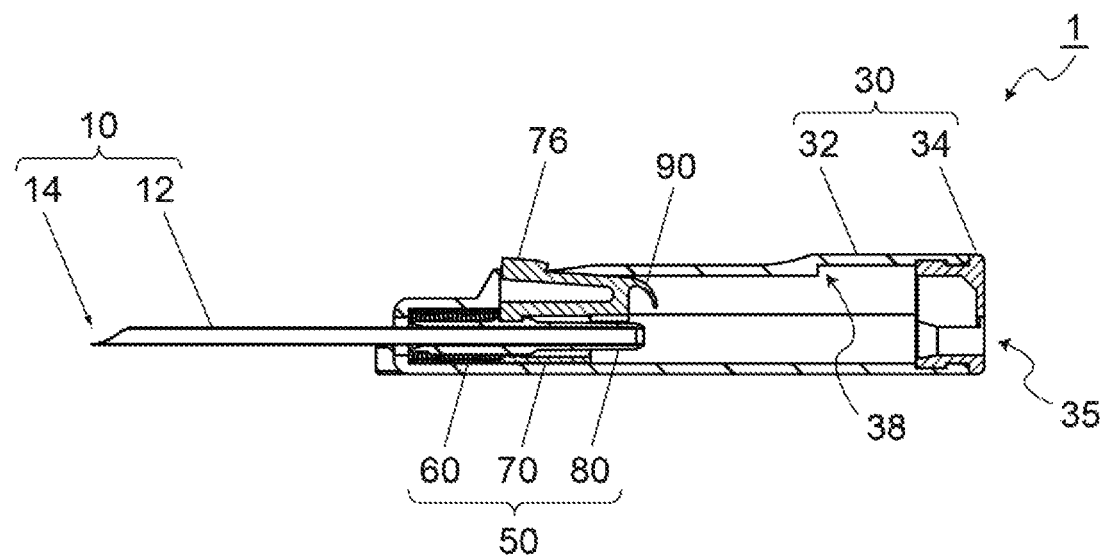
FIG. 4 is a sectional view of medical needle 1 illustrated in FIG. 3, taken along line A-A.
Figure 5:
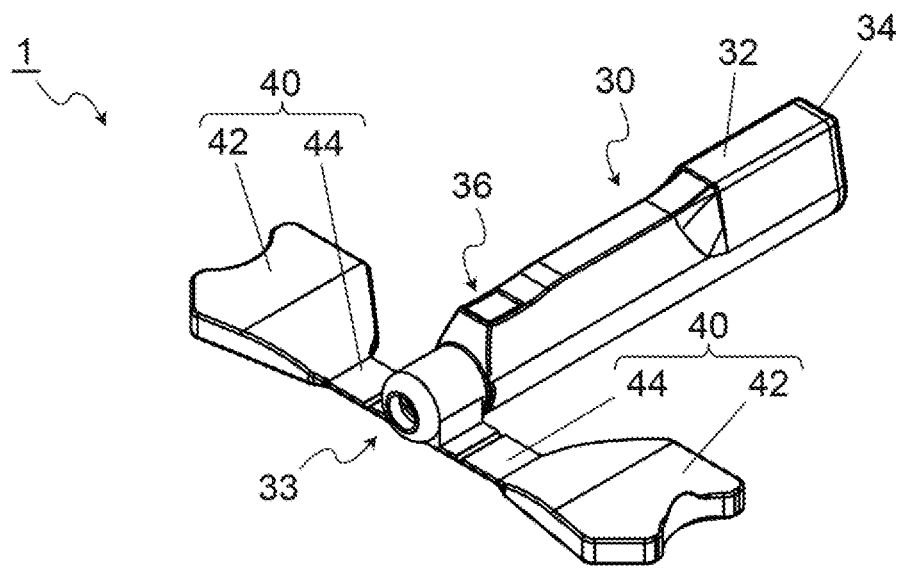
FIG. 5 is a perspective view of the whole of medical needle 1 with needle portion 10 housed in case 30.
Figure 6:
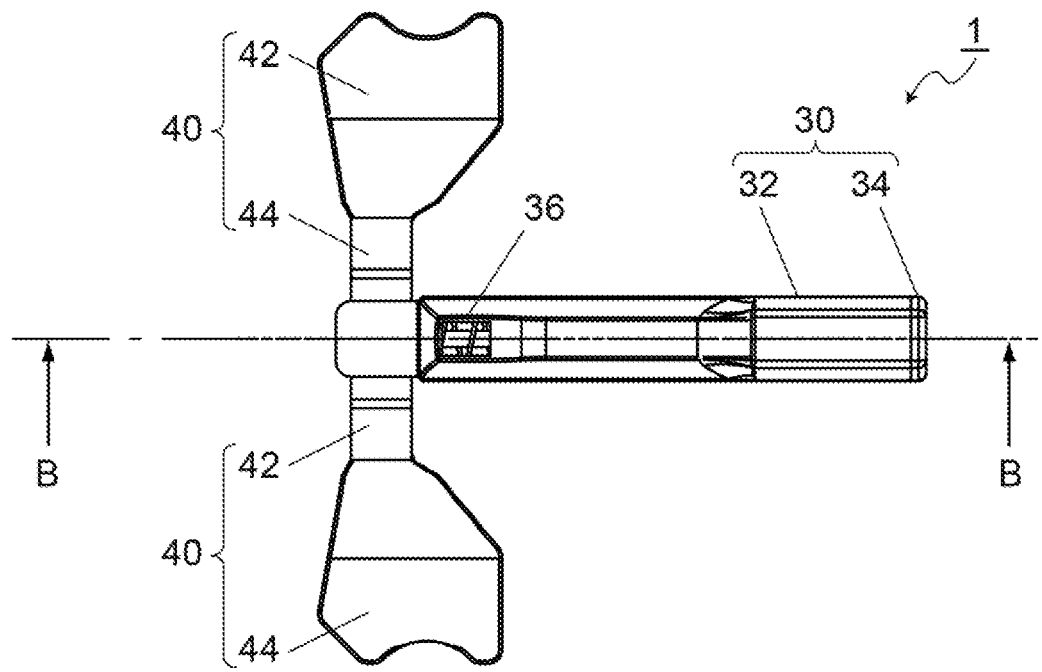
FIG. 6 is a plan view of medical needle 1 illustrated in FIG. 5.
Figure 7:
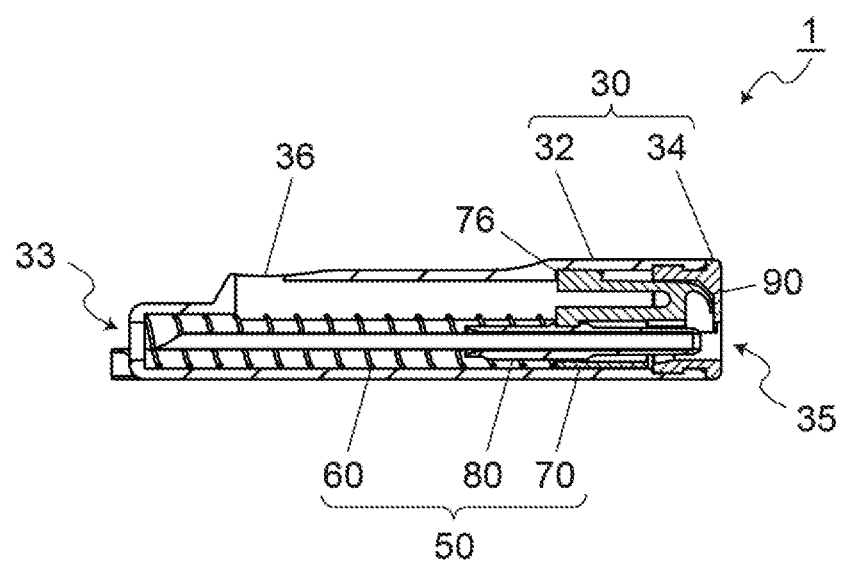
FIG. 7 is a sectional view of medical needle 1 illustrated in FIG. 6, taken along line B-B.

In the following description, a position at which needle tip 14 protrudes from case 30 by a predetermined length as illustrated in FIGS. 2 to 4 is referred to as "first position" and a position at which needle tip 14 is housed in case 30 as illustrated in FIGS. 5 to 7 is referred to as "second position."

In medical needle 1 illustrated in FIG. 3, the needle tip 14 side is referred to as "head side" and the cover 34 side as "base end side."

Medical needle 1 according to the embodiment includes, as illustrated in FIGS. 1 to 4, needle portion 10, cap 20 for covering needle portion 10, case 30 configured to be capable of housing needle portion 10, wing portion 40 provided in the head part of case 30, movement mechanism 50 that enables needle portion 10 to be housed inside case 30, and curved portion 90 provided in a part of movement mechanism 50.

Medical needle 1 is, for example, a winged needle used in a state where the needle pierces a patient's skin and is fixed thereto during blood sampling, blood transfusion, fluid transfusion and the like.

Needle portion 10 includes needle tube 12 composed of a hollow circular tube, and needle tip 14 positioned at the head of needle tube 12. Needle portion 10 is, for example, composed of a metallic material such as stainless steel, aluminum, an aluminum alloy, titanium or a titanium alloy. The base end part (the end part opposite to the needle tip) of needle tube 12 is connected to a not-illustrated tube.

Cap 20 is attached to medical needle 1 before use as illustrated in FIG. 1. Cap 20 is configured such that cap 20 can fit to the head part of case 30 while covering needle portion 10, and also can be removed from the head part of case 30.

As illustrated in FIGS. 2 to 7, case 30 includes base 32 in a shape of tube that opens at both ends, and cover 34 configured to be able to fit to the base end side opening of base 32.

At the head of base 32, opening 33 having, for example, a circular shape is provided as illustrated in FIG. 5. Opening 33 is configured such that the opening diameter thereof is set to be slightly larger than the outer diameter of needle tube 12 so that needle portion 10 can be exposed through opening 33. As illustrated in FIG. 4, a space for housing needle portion 10 is formed inside base 32 along the longitudinal direction of base 32, and thus base 32 is configured such that base 32 can house needle portion 10 inside thereof (refer to FIG. 7).

Figure 8A:
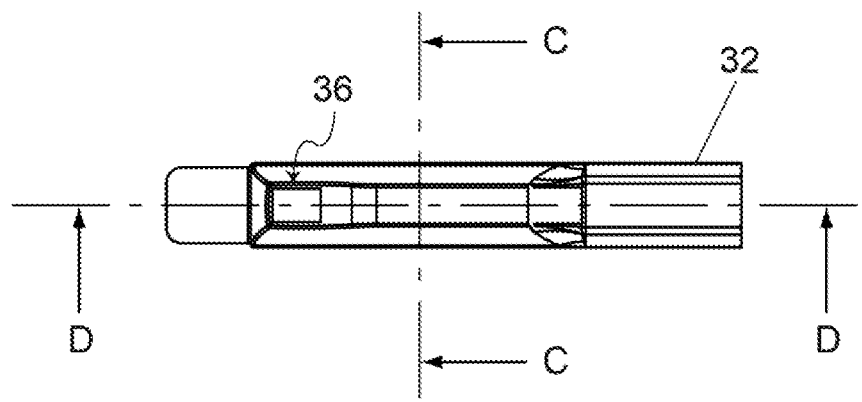
FIGS. 8A to 8C are diagrams for describing base 32.
Figure 8B:
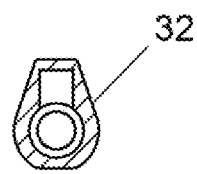
Figure 8C:
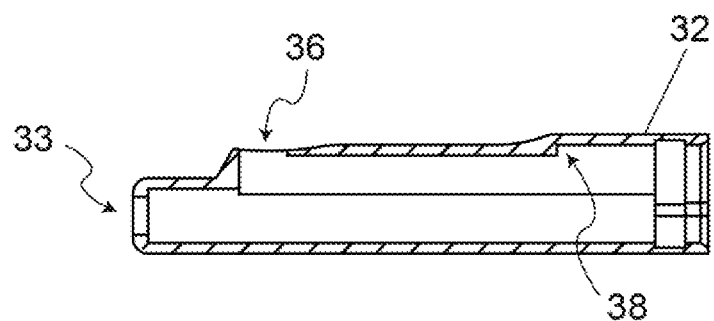

As illustrated in FIGS. 8A to 8C, first engagement portion 36 is provided in the head side part of the outer surface of base 32. First engagement portion 36 engages with below-described protrusion 76 of control portion 70 when needle portion 10 is at the first position. First engagement portion 36 is, for example, a rectangular hole that communicates with the inner space of base 32. In addition, second engagement portion 38 is provided in the base end side part (opposite to the head part) of the inner surface of base 32. Second engagement portion 38 engages with protrusion 76 of control portion 70 when needle portion 10 is at the second position. Second engagement portion 38 is, for example, a step provided in the inner surface of base 32 in such a way that the position of the inner surface of base 32 is set to become higher from the head side to the base end side of base 32.

Cover 34 includes opening 35 for allowing a tube (not illustrated) connected to needle portion 10 to pass therethrough (refer to FIG. 4).

As illustrated in FIG. 2, wing portion 40 is composed of a pair of wing members respectively connected to both side surfaces of base 32 in the head part thereof. Wing portion 40 includes grip portions 42 and thin portions 44 formed to have a thickness smaller than that of grip portions 42. Grip portion 42 is configured such that grip portion 42 can rotate by a predetermined angle with the connection part between base 32 and thin portion 44 as the axis.

As illustrated in FIGS. 4 and 7, movement mechanism 50 includes spring 60 disposed in the inner space of base 32, control portion 70 and fixing portion 80 for fixing control portion 70 to needle portion 10.

Spring 60 as the elastic member is, for example, a metal coil spring, and disposed in the inner space of base 32 in a compressed state. The head side edge of spring 60 abuts the head side part of the inner surface of base 32, and the base end side edge of spring 60 abuts the head side part of the surface of control portion 70 (refer to FIG. 11B).

Figure 9A:
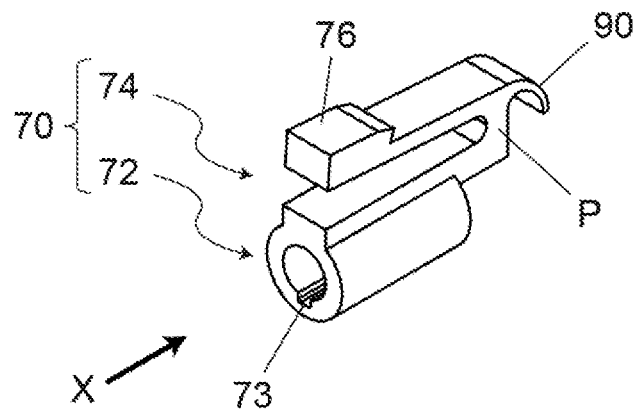
FIGS. 9A to 9C are diagrams for describing control portion 70 and curved portion 90.
Figure 9B:
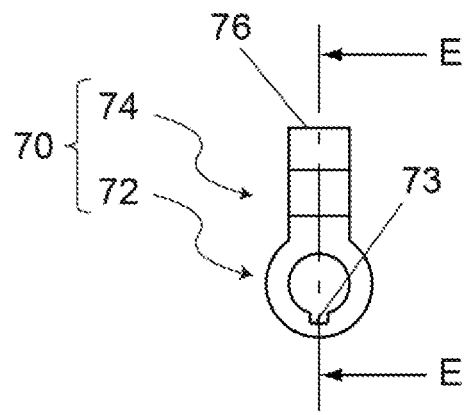
Figure 9C:
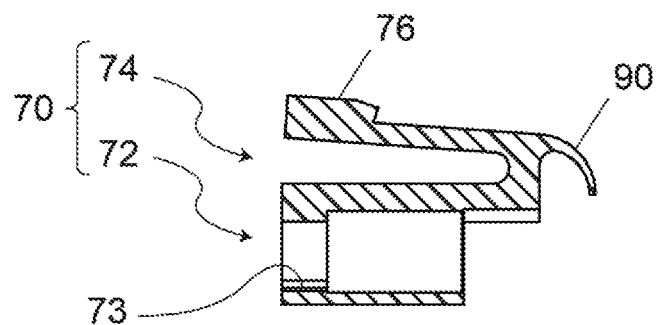

As illustrated in FIGS. 9A to 9C, control portion 70 includes connection portion 72 having, for example, a shape of a circular tube, and operation end 74 located on top of connection portion 72. The head side part of the inner surface of connection portion 72 has a smaller diameter than the rest of the inner surface of connection portion 72 has. At a position under the inner surface, i.e., the part having the smaller diameter, groove 73 is formed along the longitudinal direction.

Operation end 74 is a member located in such a way that a substantially U-shaped member is horizontally laid (i.e., in substantially dog legged shape) at a position higher than that of connection portion 72. The upper part of operation end 74 is formed in, for example, a shape of a lever (bar). While the lower part of operation end 74 is connected and fixed to connection portion 72, the head side of the upper part of operation end 74 is not fixed, and thus is a free end. At the head of the upper part of operation end 74, protrusion 76 capable of engaging with first engagement portion 36 and second engagement portion 38 is provided. The shape of protrusion 76 in plan view corresponds to the opening shape of first engagement portion 36, and is, for example, substantially rectangular. The upper part of operation end 74 is elastic in such a way that the upper part bends downward when the upper part is pressed from above, and maintains its position to keep the engagement state with first engagement portion 36 when the upper part is not pressed from above (biased upward).

Figure 10A:
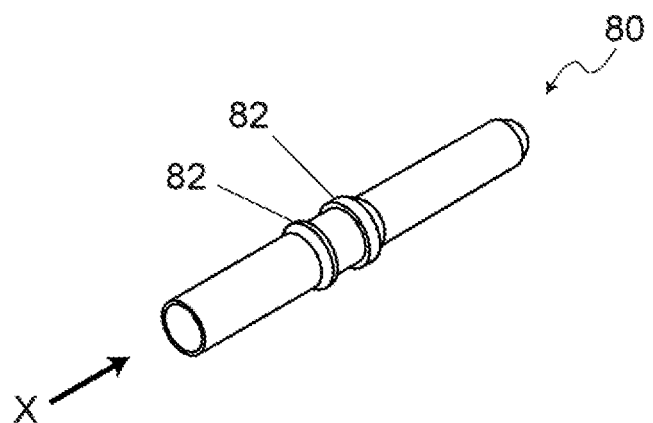
FIGS. 10A to 10C are diagrams for describing fixing portion 80.
Figure 10B:
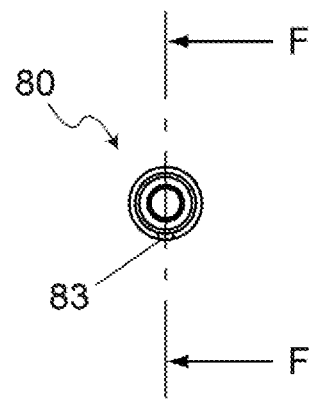
Figure 10C:
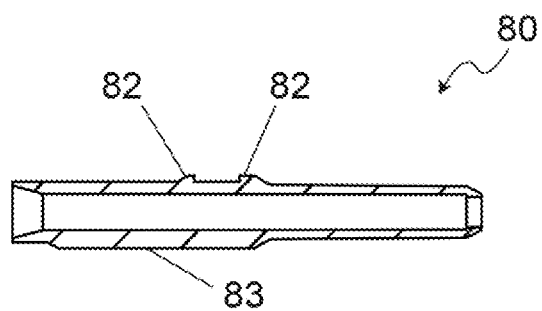

As illustrated in FIGS. 10A to 10C, fixing portion 80 is, for example, a member having a shape of a circular tube, and configured to allow needle portion 10 to be inserted therethrough. Two parallel flanges 82 are provided in the center of fixing portion 80 along the longitudinal direction. The disposition distance (distance along the longitudinal direction) of two flanges 82 is set to be substantially the same as the length of the part having the smaller diameter in connection portion 72 (the length of the part along the longitudinal direction). The outer diameter of flange 82 is set to be slightly larger than the inner diameter of the part having the smaller diameter in connection portion 72. The outer diameter of the tube of fixing portion 80 is set so that fixing portion 80 can be inserted in connection portion 72. Projection 83 corresponding to groove 73 of connection portion 72 is provided under the outer surface of fixing portion 80, and is configured to be able to fit to groove 73.

As illustrated in FIGS. 9A to 9C, curved portion 90 is connected to the base end side part of the upper part of operation end 74 (opposite to the position of protrusion 76). Curved portion 90 curves in such a way that curved portion 90 hangs down from an upper position of operation end 74 in, for example, a shape of a banana (or a horse tail), and is configured to further curve (curved so as to bent) when a force at a predetermined value or more is applied to curved portion 90.

In addition, the inner surface located in cover 34 and at the position facing curved portion 90 is, as illustrated in FIG. 4, is in a shape of a curved surface so that needle portion 10 fits (matches) curved portion 90 when needle portion 10 is at the second position (refer to FIG. 7).

Cap 20, base 32, cover 34, wing portion 40, control portion 70, fixing portion 80 and curved portion 90 are composed of a plastic material (for example, polycarbonate or polypropylene). Base 32 and wing portion 40 are integrally molded by injection molding. Control portion 70 and curved portion 90 are also integrally molded by injection molding. Cover 34 is molded separately from base 32, and then fitted and fixed to the base end side opening of base 32.

The connection structure between needle portion 10 and movement mechanism 50 will be described by using FIGS. 11A and 11B.

Figure 11A:
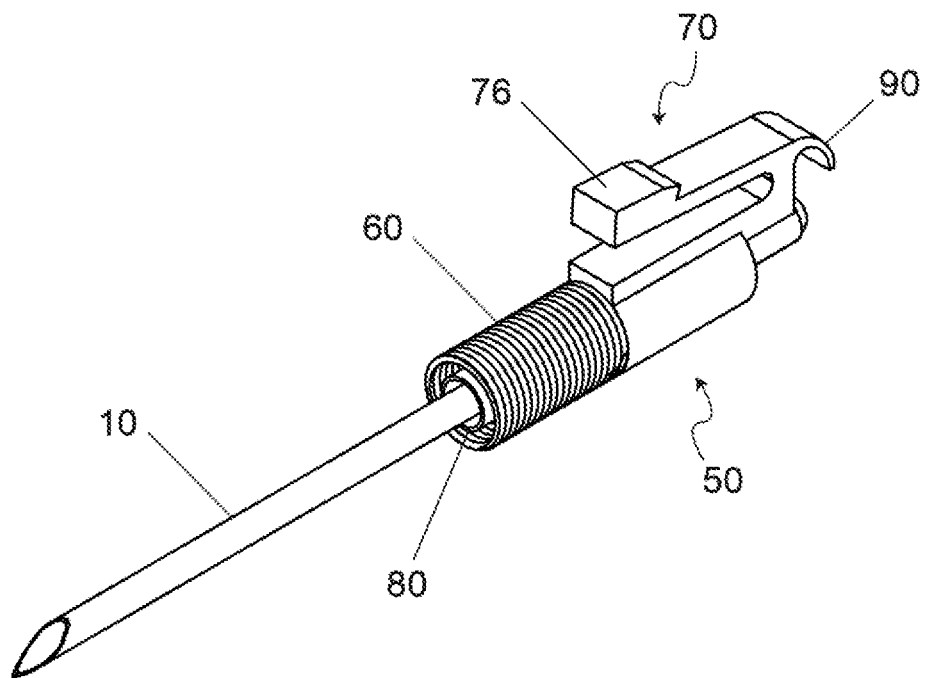
FIGS. 11A and 11B are diagrams for describing a connection structure between needle portion 10 and movement mechanism 50.
Figure 11B:
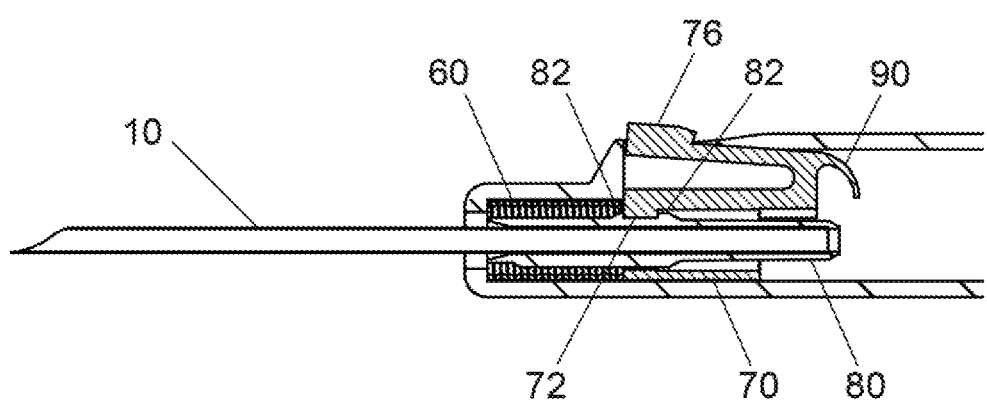

As illustrated in FIGS. 11A and 11B, needle portion 10 and fixing portion 80 are connected and fixed by using, for example, an adhesive while needle portion 10 is inserted in fixing portion 80. Fixing portion 80 is inserted into connection portion 72 of control portion 70 and fixed thereto. In this state, the part having the smaller diameter in connection portion 72 is located so as to be positioned between two flanges 82 provided on fixing portion 80, and projection 83 of fixing portion 80 is fitted to groove 73 of connection portion 72. Accordingly, the position of connection portion 72 can be fixed relative to fixing portion 80 with their positions in the longitudinal direction and the rotation direction coincide each other. Spring 60 is located outside the outer periphery of fixing portion 80 in such a way that spring 60 does not contact with needle portion 10 or fixing portion 80, but contacts with control portion 70. Spring 60 may be, for example, fixed to the head side part of the surface of control portion 70 by adhesion, or may be placed without adhesion or the like.

Hereinafter, a method for using medical needle 1 will be described.

For using medical needle 1, cap 20 is removed from medical needle 1 having cap 20 attached thereto as illustrated in FIG. 1 to expose needle tip 14 (refer to FIG. 2).

The patient's skin is then punctured with needle tip 14 while grip portion 42 of wing portion 40 is gripped. After the puncturing, grip portion 42 is unfolded to fasten medical needle 1 with a tape over grip portion 42 as necessary.

When needle tip 14 is pulled out from the patient's skin, protrusion 76 of control portion 70 is pressed to release the engagement of control portion 70 (protrusion 76) with first engagement portion 36. Control portion 70 with its engagement released is moved along with needle portion 10 from the first position to the second position by a function of spring 60, thereby pulling out needle tip 14 from the patient's skin. In this instance, the impact caused by the contact between curved portion 90 and cover 34 can be reduced by the function of curved portion 90, and also the generation of collision noise can be suppressed. In addition, the movement in control portion 70 to the head side is restricted by the engagement of protrusion 76 of control portion 70 with second engagement portion 38, and the movement in control portion 70 to the base end side is also restricted by the contact of curved portion 90 with cover 34, thereby possibly securely locking control portion 70 (thus needle portion 10) at the second position.

Alternatively, when needle tip 14 is pulled out from a patient's skin, needle tip 14 may be previously pulled out from the patient's skin and then protrusion 76 of control portion 70 may be pressed to allow needle portion 10 to be housed in case 30.

In medical needle 1 according to the embodiment configured as described above, needle portion 10 is provided with a buffer mechanism (curved portion 90) that buffers the impact caused by the contact between case 30 and movement mechanism 50 when needle portion 10 is moved to the second position. Therefore, it becomes possible to reduce the impact caused by the contact between case 30 and movement mechanism 50, and also to suppress the generation of collision noise even when a spring having relatively strong repulsion is used as an elastic member (spring 60).

Accordingly, medical needle 1 according to the embodiment is capable of reducing a user's discomfort feeling while securely housing needle tip 14 into case 30.

As medical needle 1 according to the embodiment uses the above-mentioned curved portion 90, the above-mentioned advantageous medical needle can be realized with a relatively simple configuration.

As illustrated in FIG. 7, in medical needle 1 according to the embodiment, when curved portion 90 contacts cover 34 and is thus curved, the position of protrusion 76 that is located opposite to curved portion 90 is changed upward with the connection part between curved portion 90 and operation end 74 (part indicated by sign P in FIG. 9A) as the fulcrum; therefore protrusion 76 moves closer to the inner surface of base 32 (digs into second engagement portion 38 more deeply). As protrusion 76 engages with second engagement portion 38 more strongly, control portion 70 (thus needle portion 10) can be locked at the second position more securely.

Medical needle 1 according to the embodiment includes second engagement portion 38 provided in the inner surface of base 32 where a user cannot directly touch by hand, thereby possibly further lowering the risk of erroneous piercing.

The present invention should not be limited to the above-mentioned examples in the embodiment, and the present invention may be further modified within the scope of the invention. For example, modifications as described below are also possible.

Figure 12A:
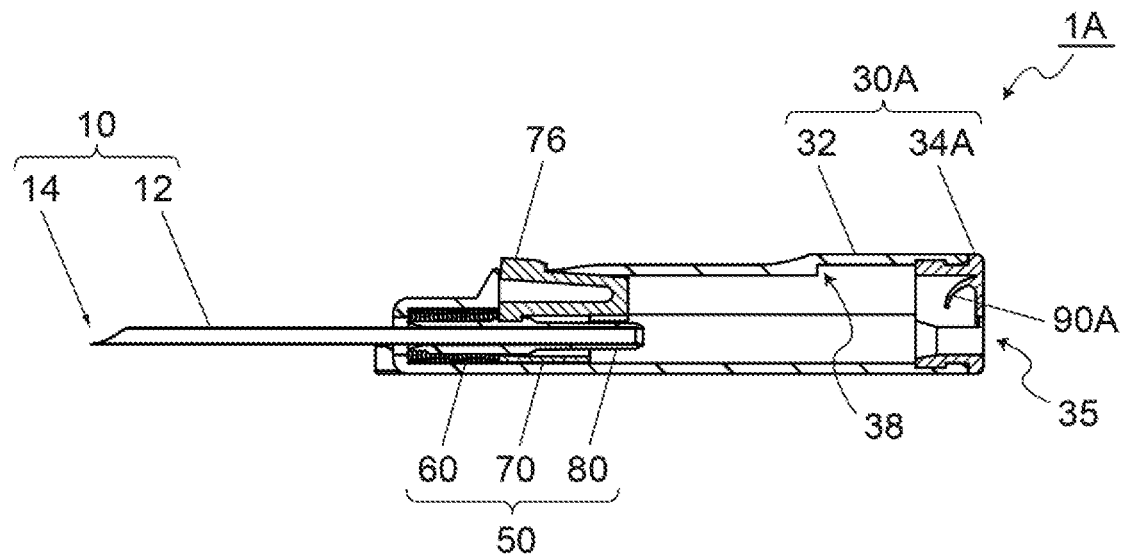
FIGS. 12A and 12B are diagrams for describing medical needle 1A according to a modification.
Figure 12B:
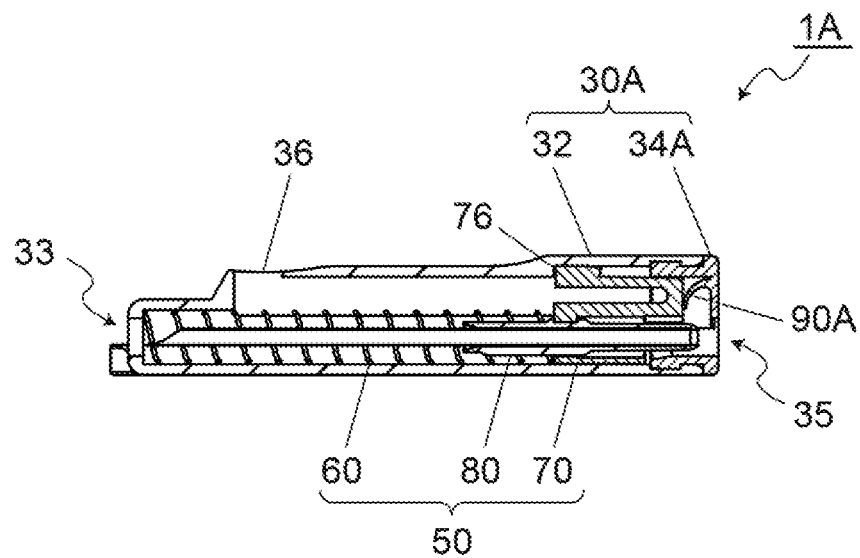

The above-mentioned embodiment describes an example in which curved portion 90 is located on the base end side of control portion 70; however, the present invention is not limited thereto. For example, as illustrated in FIGS. 12A and 12B, curved portion 90A may be provided at the position which is on the inner surface of cover 34A of case 30A and which faces control portion 70. Alternatively, though any description using drawings is omitted, a curved portion may be provided at a base end side position of a needle portion. Curved portions may be provided in both of the respective facing portions of a movement mechanism and a case.

The above-mentioned embodiment describes an example in which curved portion 90 is curved in a shape of a banana (or a horse tail); however, the present invention is not limited thereto. A curved portion may use, for example, a member that bends in a shape other than a banana shape, such as a mountain shape, a valley shape, a wave shape or the like, or a member that can be folded in a shape of a bellows. Alternatively, a spring such as a coil spring or a leaf spring, or an elastic member (another elastic member) such as rubber, a sponge or a cushion material may be used in place of the curved portion.

The above-mentioned embodiment describes an example in which needle portion 10 is composed of a metallic material; however, the present invention is not limited thereto. Needle portion 10 may be, for example, composed of a material other than a metallic material, such as a needle composed of a resin material.

The above-mentioned embodiment describes an example in which base 32 and cover 34 both located in case 30 are separately molded; however, the present invention is not limited thereto. A base and a cover may be integrally molded.

The above-mentioned embodiment describes an example in which first engagement portion 36 is a rectangular hole that communicates with the inner space of base 32; however, the present invention is not limited thereto. Another shape may be employed as long as first engagement portion 36 can engage with the control portion. Similarly, second engagement portion 38 may have another shape other than a shape of step as long as second engagement portion 38 can engage with the control portion.

The above-mentioned embodiment describes an example in which operation end 74 of control portion 70 is a substantially U-shaped (substantially dog legged shaped) member; however, the present invention is not limited thereto. Another shape such as an I shape (bar shape) may be employed. Similarly, the upper part of operation end 74 may be in a shape other than a shape of a lever (bar).

The above-mentioned embodiment describes an example in which a coil spring is used as spring 60 (elastic member) of movement mechanism 50, and the coil spring is disposed on the head side of control portion 70; however, the present invention is not limited thereto. For example, an extension spring may be disposed on base end side of the control portion. Alternatively, rubber or the like may be used in place of the spring.

The above-mentioned embodiment describes an example in which a winged needle is used in a state where the needle pierces a patient's skin and is fixed thereto; however, the present invention is not limited thereto. The present invention may be employed, for example, in an indwelling needle used for continuous intravenous drip infusion.

Figure 13A:
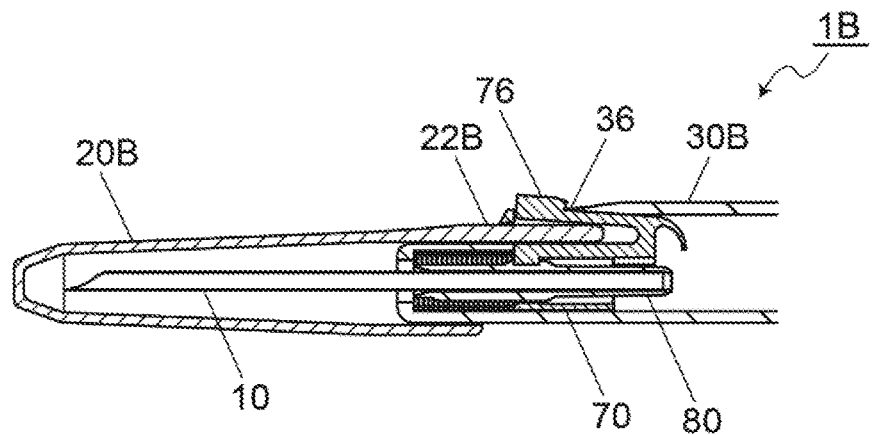
FIGS. 13A and 13B are diagrams for describing medical needle 1B according to another embodiment.
Figure 13B:
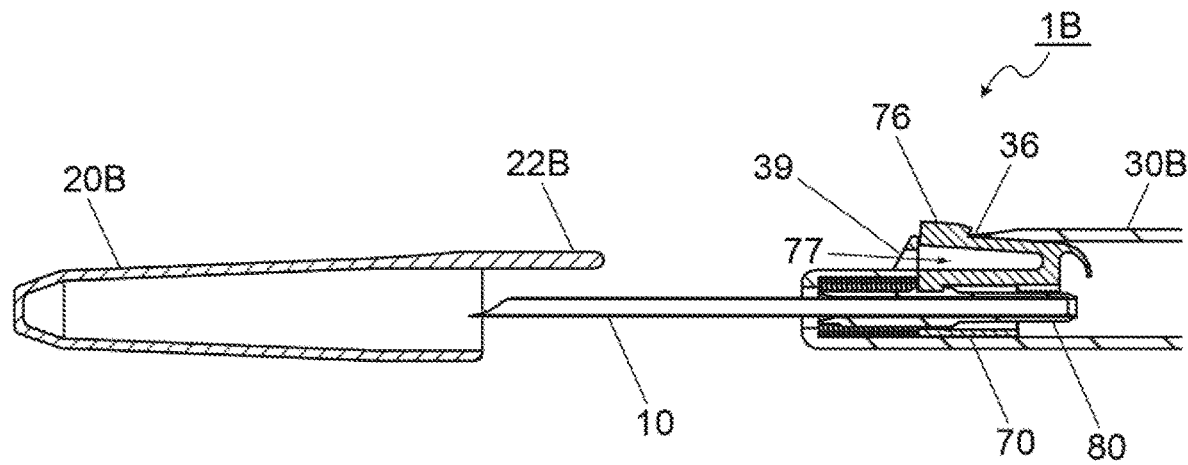

The above-mentioned embodiment is configured such that cap 20 covers protrusion 76 when cap 20 is attached so that a user does not mistakenly press protrusion 76; however, the present invention is not limited thereto. As illustrated in FIGS. 13A and 13B, for example, medical needle 1B may be configured such that cap 20B is provided with a bar shaped insertion portion 22B at the opening edge thereof, and insertion portion 22B can be inserted into space 77 that is formed below protrusion 76 via insertion opening 39 of case 30B. As illustrated in FIG. 13A, when insertion portion 22B is inserted in space 77, the downward movement of protrusion 76 is restricted, and thus the engagement between protrusion 76 and first engagement portion 36 is not released and control portion 70 does not move from the first position to the second position even when a user mistakenly presses protrusion 76. On the other hand, for housing needle portion 10 into case 30B, insertion portion 22B is removed from space 77 to release the restriction of the downward movement of protrusion 76 as illustrated in FIG. 13B. Medical needle 1B thus can be used in the same manner as the above-described medical needle 1. The shape of insertion portion 22B is not limited to a bar shape, and may be a plate shape.

REFERENCE LIST 1, 1A, 1B Medical needle
10 Needle portion
20, 20B Cap
30, 30A, 30B Case
36 First engagement portion
38 Second engagement portion
40 Wing portion
50 Movement mechanism
60 Spring
70 Control portion
80 Fixing portion
90, 90A Curved portion

What is claimed is:

1. A medical needle, comprising:
a needle portion including a needle tip at a head of the needle portion;
a case configured to be capable of exposing the needle portion from a head of the case and housing the needle portion;
a movement mechanism including an elastic member that moves the needle portion from a first position at which the needle tip protrudes from the case by a predetermined length to a second position at which the needle tip is housed in the case, the elastic member being located in the case; and
a curved portion which is provided on the movement mechanism so as to face an inner surface of the case in a longitudinal direction of the case,
wherein the movement mechanism includes:
a control portion, and
a fixing portion for fixing the control portion to the needle portion,
wherein the case includes:
a first engagement portion for engagement with the control portion when the needle portion is positioned at the first position, and
a second engagement portion for engagement with the control portion when the needle portion is positioned at the second position,
wherein the control portion has an operation end and a connection portion connected to the fixing portion,
wherein the operation end has a plate shape such that it extends along the longitudinal direction of the case, and includes a first end freely changeable and a second end connected to the connection portion,
wherein a protrusion engageable with the first engagement portion or the second engagement portion is provided at the first end,
wherein the curved portion has a curving plate shape such that the curved portion protrudes in the longitudinal direction of the case from the second end and further hangs down in an opposite direction of a protruding direction of the protrusion,
wherein the curving plate shape has a main surface with the largest area among a plurality of surfaces of the curving plate shape,
wherein the main surface is formed so as to be flush with the operation end and faces the inner surface of the case, and
wherein a position of the protrusion of the control portion changes toward the second engagement portion and engages with the second engagement portion and the main surface is in surface contact with the inner surface of the case, when the needle portion is moved to the second position by the elastic member and the curved portion contacts with the case.

2. The medical needle according to claim 1, wherein:
the elastic member includes a spring.

3. The medical needle according to claim 1, wherein:
when the engagement of the first engagement portion with the protrusion is released, the needle portion is moved from the first position to the second position by the elastic member.

4. The medical needle according to claim 1, wherein the fixing portion extends along the longitudinal direction of the case and has a circular tube shape through which the needle portion is inserted, and is connected to a part of the connection portion at the center of the fixing portion.

5. A medical needle, comprising:
a needle portion including a needle tip at a head of the needle portion;
a case configured to be capable of exposing the needle portion from a head of the case and housing the needle portion;
a movement mechanism including an elastic member that moves the needle portion from a first position at which the needle tip protrudes from the case by a predetermined length to a second position at which the needle tip is housed in the case, the elastic member being located in the case; and
a curved portion which is provided on the movement mechanism so as to face an inner surface of the case in a longitudinal direction of the case,
wherein the movement mechanism includes:
a control portion, and
a fixing portion for fixing the control portion to the needle portion,
wherein the case includes:
a first engagement portion for engagement with the control portion when the needle portion is positioned at the first position, and
a second engagement portion for engagement with the control portion when the needle portion is positioned at the second position,
wherein the control portion has a plate shape such that it extends along the longitudinal direction of the case, and includes a first end freely changeable and a second end connected to the fixing portion,
wherein a protrusion engageable with the first engagement portion or the second engagement portion is provided at the first end,
wherein the curved portion has a curving plate shape such that the curved portion protrudes in the longitudinal direction of the case from the second end and further hangs down in an opposite direction of a protruding direction of the protrusion,
wherein a main surface of the curved portion is formed so as to be flush with the control portion and faces the inner surface of the case, and
wherein a position of the protrusion of the control portion changes toward the second engagement portion and engages with the second engagement portion and the main surface of the curved portion is in surface contact with the inner surface of the case, when the needle portion is moved to the second position by the elastic member and the curved portion contacts with the case.

* * * * *